(12) United States Patent
Malik

(10) Patent No.: US 7,419,655 B2
(45) Date of Patent: Sep. 2, 2008

(54) SKIN CARE PRODUCTS

(75) Inventor: Sohail Malik, Athens, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/241,406

(22) Filed: Sep. 11, 2002

(65) Prior Publication Data

US 2004/0047827 A1 Mar. 11, 2004

(51) Int. Cl.
*A61K 8/67* (2006.01)
*A61K 8/73* (2006.01)

(52) U.S. Cl. .................. 424/70.13; 514/55; 514/356; 514/474

(58) Field of Classification Search .............. 514/55, 514/351–356, 474
See application file for complete search history.

(56) References Cited

U.S. PATENT DOCUMENTS

| | | | |
|---|---|---|---|
| 2,831,854 A | 4/1958 | Tucker et al. .............. 260/234 |
| 3,963,699 A | 6/1976 | Rizzi et al. ................ 260/234 |
| 4,005,195 A | 1/1977 | Jandacek .................. 424/180 |
| 4,005,196 A | 1/1977 | Jandacek et al. ........... 424/180 |
| 4,517,360 A | 5/1985 | Volpenhein ............... 536/119 |
| 4,518,772 A | 5/1985 | Volpenhein ............... 536/119 |
| 4,797,300 A | 1/1989 | Jandacek et al. ........... 426/549 |
| 4,800,197 A | 1/1989 | Kowcz et al. ............. 514/162 |
| 4,976,953 A | 12/1990 | Orr et al. .................. 424/47 |
| 5,306,515 A | 4/1994 | Letton et al. .............. 426/531 |
| 5,306,516 A | 4/1994 | Letton et al. .............. 426/531 |
| 5,736,532 A * | 4/1998 | Furda ...................... 514/55 |
| 5,843,411 A * | 12/1998 | Hernandez et al. ......... 424/59 |
| 5,968,528 A * | 10/1999 | Deckner et al. ........... 424/401 |
| 6,267,975 B1 | 7/2001 | Smith, III et al. .......... 424/401 |
| 2001/0024655 A1 | 9/2001 | Schneider et al. .......... 424/401 |
| 2002/0111576 A1 * | 8/2002 | Greene et al. ............. 602/42 |

FOREIGN PATENT DOCUMENTS

| | | |
|---|---|---|
| JP | 10-001414 | 1/1998 |
| KR | 2002011594 | 2/2002 |
| WO | WO-00/28961 | 5/2000 |

OTHER PUBLICATIONS

"Application of Emulsion Stability Theories to Mobile and Semisolid Oil-in-Water Emulsions", *Cosmetics & Toiletries*, 101, (1986),73-92.
Oikarinen,"The Aging of Skin: Chronoaging Versus Photoaging", *Photodermatology, Photoimmunology, Photomedicine*, 7, (1990),3-4.
Sagarin, *Cosmetics Science and Technology 2nd Edition*, 2, (1972),443-465.
Sagarin, *Cosmetics, Science, and Technology 2nd Edition*, 1, (1972),32-43.
Sagarin, *Cosmetics, Science, and Technology 2nd Edition*, 1, (1972),72-73.
Wenner, W., "The Reaction of L-Ascorbic & D-losascorbic Acid with Nicotinic Acid & Its Amide", *Journal of Organic Chemistry*, 14, (1949),22-26.
*McCutcheon's Detergents & Emulsifiers, North American Edition*, Allured Publishing Corporation,(1986).
US 5,305,514, 04/1994, Letton et al. (withdrawn)

* cited by examiner

*Primary Examiner*—Leigh C Maier
(74) *Attorney, Agent, or Firm*—Armstrong Teasdale LLC

(57) ABSTRACT

The invention provides compositions and methods for conditioning the skin and reversing the effects of aging on the skin.

5 Claims, 2 Drawing Sheets

SKIN CARE PRODUCTS

FIELD OF THE INVENTION

The present invention relates to compositions containing chitosan, niacinamide and ascorbic acid that can counteract the effects of aging on the skin. Such compositions can increase the proliferation of fibroblasts.

BACKGROUND OF THE INVENTION

Skin is subject to insults by many extrinsic and intrinsic factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin. Whether extrinsic or intrinsic, these factors result in visible signs of skin aging and environmental damage, such as wrinkling and other forms of roughness (including increased pore size, flaking and skin lines), and other histological changes associated with skin aging or damage. To many people, skin wrinkles are a reminder of the disappearance of youth. As a result, the elimination of wrinkles has become a booming business in youth-conscious societies. Treatments range from cosmetic creams and moisturizers to various forms of cosmetic surgery.

Such extrinsic or intrinsic factors may result in the thinning and general degradation of the skin. For example, as the skin naturally ages, there is a reduction in the cells and blood vessels that supply the skin. There is also a flattening of the dermal-epidermal junction that results in weaker mechanical resistance of this junction. See, for example, Oikarinen, "The Aging of Skin: Chronoaging Versus Photoaging," Photodermatol. Photoimmunol. Photomed., vol. 7, pp. 3-4, 1990, which is incorporated by reference herein in its entirety.

Accordingly, new compositions for regulating and minimizing the effects of aging on the skin are needed.

SUMMARY OF THE INVENTION

The invention provides compositions and methods for reducing the effects of aging on the skin. Such compositions and methods, for example, can reduce or efface the visibility of the fine lines, wrinkles, and other forms of uneven or rough surface texture associated with aged or photodamaged skin. These compositions are non-toxic and can help maintain or restore healthy functioning in skin tissues.

Thus, the present invention is directed to a composition comprising an effective amount of chitosan, ascorbic acid, and a vitamin $B_3$ compound, especially niacinamide. Such a composition can counteract the effects of aging on the skin.

The invention is also directed to methods of counteracting the effects of aging on the skin by administering to a mammal a composition comprising an effective amount of chitosan, ascorbic acid, and a vitamin $B_3$ compound, especially niacinamide. In general, administration is topical. These methods can inter alia modulate or alleviate wrinkling, photodamage, unevenness and dryness in the skin of a mammal.

The invention further provides a method for increasing growth of fibroblasts by contacting the fibroblasts with a composition comprising an effective amount of chitosan, ascorbic acid, and a vitamin $B_3$ compound, especially niacinamide.

Compositions and methods of the invention prophylactically and/or therapeutically regulate the mammalian skin condition (especially of human skin, more especially facial skin) and signs of mammalian skin aging by regulating visible and/or tactile discontinuities in mammalian skin texture, including fine lines, wrinkles, enlarged pores, roughness and other skin texture discontinuities associated with aged skin with reduced irritation and dryness. Compositions and methods of the invention are gentle, non-irritating and non-drying to the skin. Such compositions and methods can prevent or treat wrinkling, dryness and/or enhance the health and vibrancy of skin tissues.

DETAILED DESCRIPTION OF THE INVENTION

Figure 1:
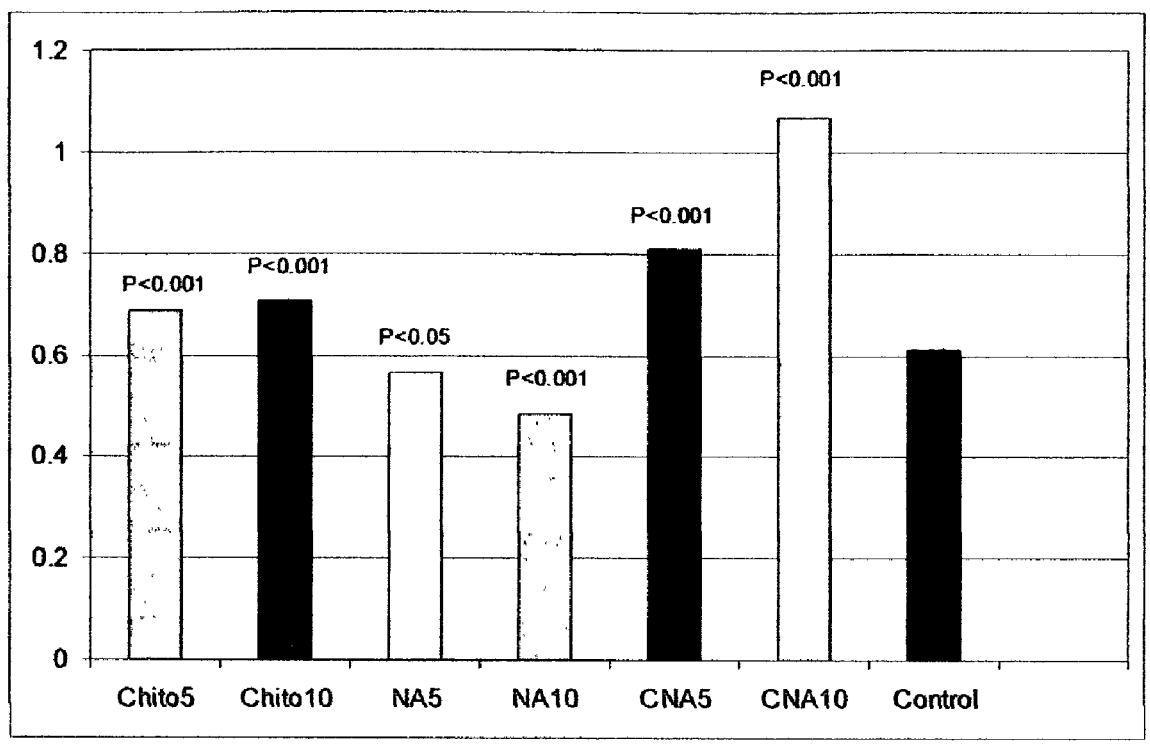
FIG. 1 provides a bar graph illustrating that the addition of chitosan, ascorbic acid, and niacinamide (CNA) leads to increased growth of fibroblasts in a dose-dependent manner. The cell density of fibroblasts receiving equimolar chitosan, ascorbic acid, and niacinamide (5 µl labeled CNA5; 10 µl labeled CNA10) was compared to control fibroblast cells that received serum-free medium cells (Control), fibroblasts receiving 0.1649 M niacinamide alone (5 µl labeled NA5; 10 µl labeled NA10) and fibroblasts receiving 0.1649 M chitosan alone (5 µl labeled Chito5; 10 µl labeled Chtio10). As shown, the combination of chitosan, ascorbic acid, and niacinamide (CNA) leads to greatly increased cellular growth of fibroblasts, suggesting that this combination acts synergistically to increase the growth of fibroblasts.
Figure 2:
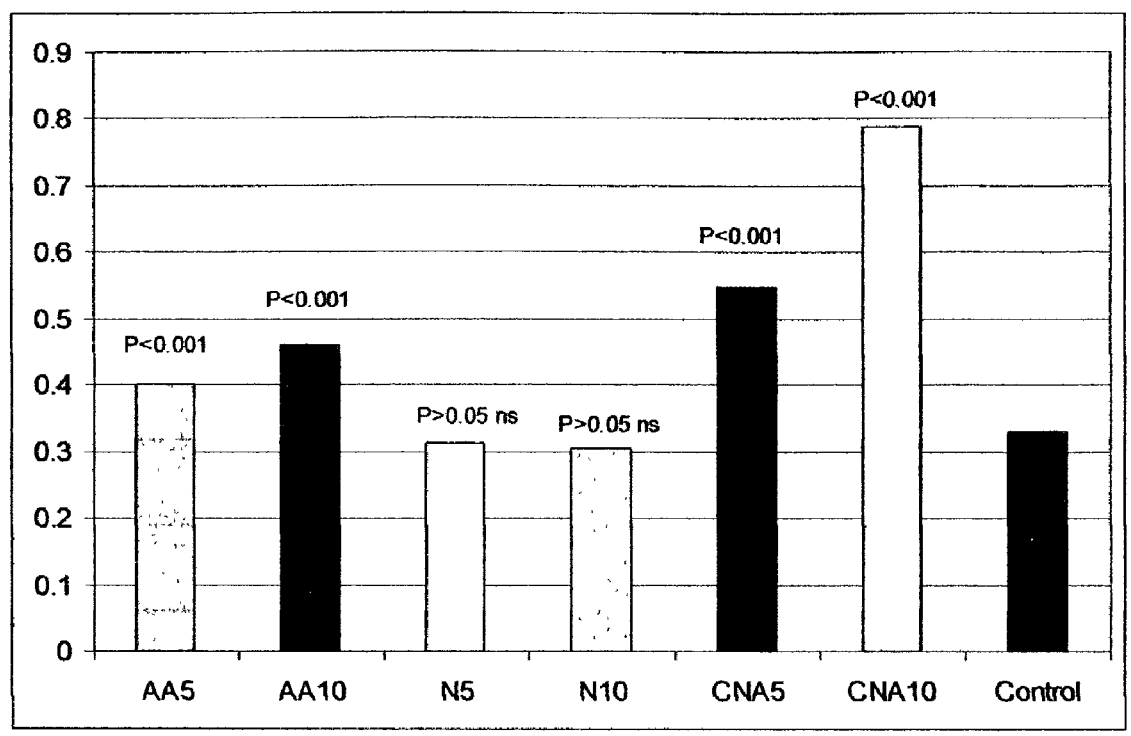
FIG. 2 provides a bar graph that also illustrates that the addition of chitosan, ascorbic acid, and niacinamide (CNA) leads to increased growth of fibroblasts in a dose-dependent manner. The cell density of fibroblasts receiving equimolar chitosan, ascorbic acid, and niacinamide (5 µl labeled CNA5; 10 µl labeled CNA10) is compared to control fibroblast cells that received serum-free medium cells (Control), fibroblasts receiving 0.1649 M niacinamide alone (5 µl labeled N5; 10 µl labeled N10) and fibroblasts receiving 0.1649 M ascorbic acid alone (5 µl labeled AA5; 10 µl labeled AA10). As shown, the combination of chitosan, ascorbic acid, and niacinamide (CNA) leads to greatly increased cellular growth of fibroblasts, suggesting that this combination acts synergistically to increase the growth of fibroblasts.

The invention provides compositions and methods for treating and conditioning the skin. Compositions of the invention comprise an effective amount of chitosan, ascorbic acid, and a vitamin $B_3$ compound, especially niacinamide. The invention further provides methods of counteracting the effects of aging on the skin by administering to a mammal a composition comprising an effective amount of chitosan, ascorbic acid, and a vitamin $B_3$ compound, especially niacinamide. Administration of the compositions of the invention can increase the proliferation of fibroblasts, and provide new healthy skin tissues that do not suffer from effects of aging such as fine lines, wrinkles, enlarged pores, roughness and skin texture discontinuities. Advantages of this invention include inexpensive, readily available active compounds that are readily absorbed and used by the body and that simply and effectively enhance the natural resiliency of the skin.

Definitions

The term "dermatologically-acceptable," as used herein, means that the compositions or components thereof so described are suitable for use in contact with human skin without undue toxicity, incompatibility, instability, allergic response, and the like.

"Regulating skin condition" includes prophylactically regulating and/or therapeutically regulating skin condition, including visible and/or tactile discontinuities in skin. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, discontinuities in skin. Regulating skin condition involves improving skin appearance and/or feel. Visible and/or tactile discontinuities in the skin that are treated by the present compositions and methods are generally undesired visible and/or tactile discontinuities.

The term "safe and effective amount" as used herein means an amount of a compound or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound judgment of the skilled artisan. The term "topical application", as used herein, means to apply or spread the compositions of the present invention onto the surface of the skin.

Skin

The skin consists of several layers, including the epidermis, the dermis and the subcutaneous tissue. The outermost layer, known as the dermis, also has several layers, including the stratum corneum, the stratum granulosum, the squamous cell layer, and the basal cell layer.

Through a process known as desquamation, the epidermis has the ability to constantly renew itself by shedding the flattened dead skin cells composing the stratum corneum. However, over time this normal metabolic process slows down, calling for skin compositions that effectively peel, exfoliate and remove these dead cells and related impurities, accelerating desquamation that is a part of the natural cell renewal cycle of the skin.

The stratum corneum is the outer coating of the epidermis. It consists of compacted dead cells called keratinocytes that are composed of keratin, a dried out protein. This is the layer of skin that is felt and seen and can be characterized, for example, as smooth, soft, oily or flaky. Cells of the basal cell layer take about two to four weeks to migrate upwards through four epidermal layers until they reach the top layer, the stratum corn. There they are compacted and under optimal circumstances, shed over a period of two to six weeks.

The usual turnover time of the epidermis, namely the time it takes for cells to migrate from the basal cell layer to the point of being shed from the stratum corneum, is about four to eight weeks. However, with aging, the stratum corneum begins to lose its dynamic ability to constantly renew. Young skin renews its surface layers every two to three weeks, whereas mature skin may take twice as along to be renewed.

Many individuals who have had a good deal of sun exposure in childhood will show the following gross cutaneous alterations in later adult life: wrinkling, leatheriness, yellowing, looseness, roughness, dryness, mottling (hyperpigmentation) and various premalignant growths (often subclinical). These changes are most prominent in light-skinned persons who burn easily and tan poorly. These cumulative effects of sunlight are often referred to as photoaging or photodamage. Although the anatomical degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness and loss of elasticity are very late changes.

Uses for the Present Compositions

The present compositions are designed to accelerate the turnover of cells within the skin by encouraging new cells to form and facilitating desquamation of old cells, thereby restoring the skin's freshness and youthful appearance. The compositions of the invention comprise an effective amount of chitosan, ascorbic acid, and a vitamin $B_3$ compound, especially niacinamide.

The compositions of the present invention are useful for regulating skin condition and reducing signs of skin aging. "Signs of skin aging" include, but are not limited to, undesired visibly and tactilely perceptible manifestations as well as any other macro or micro effects of skin aging. Such signs may be induced or caused by intrinsic factors or extrinsic factors, for example, chronological aging and/or environmental damage. These signs may include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin., including visible and/or tactile discontinuities in skin, especially the skin surface. Such discontinuities may arise from internal and/or external factors, and include signs of skin aging such as lines, wrinkles, enlarged pores and the like. As used herein, prophylactically regulating such signs of skin aging includes delaying, minimizing and/or preventing signs of skin aging. As used herein, therapeutically regulating such signs includes ameliorating, e.g., diminishing, minimizing and/or effacing signs of skin aging.

It is to be understood that the present invention is not to be limited to regulation of the above mentioned "signs of skin aging" which arise due to mechanisms associated with skin aging, but is intended to include regulation of said signs irrespective of the mechanism of origin. As used herein, "regulating skin condition" is intended to include regulation of such signs irrespective of the mechanism of origin.

The present invention is especially useful for therapeutically regulating visible and/or tactile discontinuities in mammalian skin texture, including texture discontinuities related to skin aging while reducing the irritation and dryness associated with such treatments. As used herein, therapeutically regulating such discontinuities includes ameliorating, e.g., diminishing, minimizing and/or effacing visible and/or tactile discontinuities in the texture of mammalian skin, to thereby provide improved skin appearance and/or feel, e.g., a smoother, more even appearance and/or feel. Such visible and/or tactile discontinuities in skin texture include crevices, bumps, pores, fine lines, wrinkles, scales, flakes and/or other forms of textural unevenness or roughness associated with skin aging. For example, the length, depth, and/or other dimension of lines and/or wrinkles are decreased, the apparent diameter of pores decreases, or the apparent height of tissue immediately proximate to pore openings approaches that of the interadnexal skin.

The present invention is also especially useful for prophylactically regulating visible and/or tactile discontinuities in mammalian skin texture, including texture discontinuities associated with skin aging. As used herein, prophylactically regulating such discontinuities includes delaying, minimizing and/or preventing visible and/or tactile discontinuities in the texture of mammalian skin, to thereby provide improved skin appearance and/or feel, e.g., a smoother, more even appearance and/or feel.

Vitamin $B_3$ Component

The compositions of the present invention comprise a safe and effective amount of a natural or synthetic vitamin $B_3$ compound. The compositions of the present invention preferably comprise a mixture solid active ingredients containing from about 0.01% to about 60%, more preferably from about 1% to about 50%, even more preferably from about 10% to about 40%, and still more preferably from about 20% to about 30% of the vitamin $B_3$ compound. These amounts are provided as weight ratios of the active ingredients. The total amount of active ingredients provided in the composition can vary. Hence, the total amount of vitamin $B_3$ compound in the composition can also vary and the total weight percentage of the vitamin $B_3$ compound within the composition can be outside these percentage ranges so long as a balance of active ingredients is achieved. Moreover, the composition can be provided as a solid, liquid, suspension, emulsion or as any other convenient form selected by one of skill in the art.

As used herein, "vitamin $B_3$ compound" means a compound having the formula:

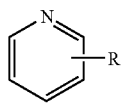

wherein R is —$CONH_2$ (e.g., niacinamide), —COOH (e.g., nicotinic acid) or —$CH_2OH$ (e.g., nicotinyl alcohol), derivatives thereof, and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid include nicotinic acid esters of $C_1$-$C_{22}$, preferably $C_1$-$C_{16}$, more preferably $C_1$-$C_6$ alcohols. The alcohols are suitably straight-chain or branched chain, cyclic or acyclic, saturated or unsaturated (including aromatic), and substituted or unsubstituted. The esters are preferably non-rubicient. As used herein, "non-rubicient" means that the ester does not commonly yield a visible flushing response after application to the skin in the subject compositions (the majority of the general population would not experience a visible flushing response, although such compounds may cause vasodilation not visible to the naked eye). Non-vasodilating esters of nicotinic acid include tocopherol nicotinate and inositol hexanicotinate; tocopherol nicotinate is preferred.

Exemplary nicotinyl alcohol esters include nicotinyl alcohol esters of the carboxylic acids salicylic acid, acetic acid, glycolic acid, palmitic acid and the like. Other non-limiting examples of vitamin $B_3$ compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Examples of the above vitamin $B_3$ compounds are commercially available from a number of sources, e.g., the Sigma Chemical Company (St. Louis, Mo.); ICN Biomedical, Inc. (Irvin, Calif.) and Aldrich Chemical Company (Milwaukee, Wis.).

One or more vitamin $B_3$ compounds may be used herein. Desirable vitamin $B_3$ compounds are niacinamide and tocopherol nicotinate. Niacinamide is highly desirable.

Salts, derivatives, and salt derivatives of niacinamide are those having substantially the same efficacy as niacinamide in the methods of regulating skin condition described herein. Nonlimiting examples of salts of the vitamin $B_3$ compound useful herein include organic or inorganic salts, such as inorganic salts with anionic inorganic species (e.g., chloride, bromide, iodide, carbonate, preferably chloride), and organic carboxylic acid salts (including mono-, di- and tri-$C_1$-$C_{18}$ carboxylic acid salts, e.g., acetate, salicylate, glycolate, lactate, malate, citrate, preferably monocarboxylic acid salts such as acetate). These and other salts of the vitamin $B_3$ compound can be prepared by the skilled artisan, for example, as described by W. Wenner, "The Reaction of L-Ascorbic and D-Iosascorbic Acid with Nicotinic Acid and Its Amide", J. Organic Chemistry, VOL. 14, 22-26 (1949), which is incorporated herein by reference. Wenner describes the synthesis of the ascorbic acid salt of niacinamide.

In one embodiment, the ring nitrogen of the vitamin $B_3$ compound is substantially chemically free or "uncomplexed" (e.g., unbound and/or unhindered). Such a chemically free state is desired after delivery to the skin becomes substantially chemically free. Hence, if the composition contains the vitamin $B_3$ compound in a salt or otherwise complexed form, such complex is substantially reversible, or essentially reversible, upon delivery of the composition to the skin. For example, such complex should be substantially reversible at a pH of from about 5.0 to about 6.0. Such reversibility can be readily determined by one having ordinary skill in the art. Exemplary approaches to minimizing or preventing the formation of undesirable complexes include omission of materials which form substantially irreversible or other complexes with the vitamin $B_3$ compound, pH adjustment, ionic strength adjustment, the use of surfactants, and formulating wherein the vitamin $B_3$ compound and materials which complex therewith are in different phases. Such approaches are well within the level of ordinary skill in the art.

Thus, in some embodiments, the vitamin $B_3$ compound contains a limited amount of the salt form and is substantially free of salts of a vitamin $B_3$ compound. The vitamin $B_3$ compound can contain less than about 50%, less than 40%, less than 30%, or less than 25%, of such salt. The vitamin $B_3$ compound in the compositions hereof having a pH of from about 4 to about 7 typically contain less than about 50% of the salt form.

The vitamin $B_3$ compound may be included as the substantially pure material, or as an extract obtained by suitable physical and/or chemical isolation from natural (e.g., plant) sources. The vitamin $B_3$ compound is preferably substantially pure, more preferably essentially pure.

Chitosan Component

Chitosan is a high molecular weight linear polymer composed of 2-amino-2-deoxy-D-gluose obtained by deacetylation of chitin in concentrated alkali. The molecular weight of commercially available chitosan is typically between about 100,000 and about 2,000,000. Chitosan is non-toxic and biodegradable. Chitosan is fungicidal for both animal and plant pathogens so long as chitosan is not a component of the fungal cell wall. Films of chitosan salts are useful in healing wounds.

The compositions of the present invention comprise a safe and effective amount of chitosan. The compositions of the present invention preferably comprise a mixture of active ingredients containing from about 0.1% to about 80%, more preferably from about 10% to about 70%, even more preferably from about 25% to about 65%, and still more preferably from about 40% to about 60% of chitosan. These amounts are provided as weight ratios of the active ingredients. The total amount of active ingredients provided in the composition can vary. Hence, the total amount of chitosan in the composition can also vary and the total weight percentage of chitosan within the composition can be outside these percentage ranges so long as a balance of active ingredients is achieved. Moreover, the composition can be provided as a solid, liquid, suspension, emulsion or as any other convenient form selected by one of skill in the art.

Chitosan can be obtained by heating chitin generally contained in outer skin of Crustacea such as crabs or prawns, with concentrated alkali to cause deacetylation. In general, the chitosan obtained has a molecular weight of 5,000 to 1,000,000, an intrinsic viscosity (30° C., 0.2 M acetic acid, 0.1M sodium acetate) of 0.25 to 20 dl/g-chitosan and, a colloid equivalent (a cationic density) of 1.0 to 6.2 meq/g-chitosan. The degree of deacetylation is sufficient if the deacetylated chitin can be dissolved with acid. Such a degree of deacetylation is, for example, approximately 50 to 100 mol %. A mean grain diameter of chitosan can be about 9 to 300 mesh.

Any acid available to one of skill in the art can be used for dissolving chitosan, so long as it can facilitate formation of an aqueous solution of chitosan. Representative examples of such acids include organic acids such as acetic acid, formic acid, propionic acid, butyric acid, valeric acid, isopropionic acid, isobutyric acid, isovaleric acid, benzoic acid, cinnamic acid, salicylic acid, anthranylic acid, phthalic acid, and the like, as well as mineral acids such as hydrochloric acid, nitric acid, and the like.

In the case where insoluble matters are present in the acidic aqueous solution of chitosan, the solution is filtered through a glass filter or a metal mesh such as stainless, copper, etc.

Vitamin C Component

The compositions of the present invention can comprise a safe and effective amount of ascorbic acid or a derivative thereof. The compositions of the present invention comprise a mixture of solid active ingredients containing from about 0.01% to about 60%, more preferably from about 1% to about 50%, even more preferably from about 10% to about 40%, and still more preferably from about 20% to about 30% of vitamin C. These amounts are provided as weight ratios of the active ingredients. The total amount of active ingredients provided in the composition can vary. Hence, the total amount of vitamin C compound in the composition can also vary and the total weight percentage of the vitamin C compound within the composition can be outside these percentage ranges so long as a balance of active ingredients is achieved. Moreover, the composition can be provided as a solid, liquid, suspension, emulsion or as any other convenient form selected by one of skill in the art.

Preferably, the vitamin C (ascorbic acid) is L-ascorbic acid. Nonlimiting examples of useful derivatives of ascrobic acid include magnesium ascorbyl phosphate and ascorbyl glucosamine.

Other Components

Other components that can be included in the compositions of the invention include conditioning components, aloe vera, and additional vitamins (e.g. vitamin E).

Conditioning components are preferably selected from the group consisting of emollients and humectants and mixtures thereof. The conditioning agent is present at a level of from about 1% to about 99%, preferably from about 1% to about 50%, more preferably from about 2% to about 30% and most preferably from about 5% to about 25%.

A variety of emollients may be employed to yield the conditioning component of the present invention. These emollients may be selected from one or more of the following classes: triglyceride esters that include, but are not limited to, vegetable and animal fats and oils such as castor oil, cocoa butter, safflower oil, cottonseed oil, corn oil, olive oil, cod liver oil, almond oil, avocado oil, palm oil, sesame oil, squalene, kikui oil and soybean oil; acetoglyceride esters, such as acetylated monoglycerides; alkyl esters of fatty acids having 10 to 20 carbon atoms which include, but are not limited to, methyl, isopropyl, and butyl esters of fatty acids such as hexyl laurate, isohexyl laurate, isohexyl palmitate, isopropyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated sorbitol lanolin, and liquid and semisolid lanolin absorption bases; polyhydric alcohol esters such as ethylene glycol mono and di-fatty acid esters, diethylene glycol mono-and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; Wax esters such as beeswax, spermaceti, myristyl myristate, stearyl stearate; forming a mixture of ether esters; Vegetable waxes including, but not limited to, carnauba and candelilla waxes; and cholesterol fatty acid esters. Also useful are the propoxylated glycerols described in U.S. Pat. No. 4,976,953, which is description is incorporated herein by reference.

Other useful emollients include various $C_1$-$C_{30}$ monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifing carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifing carboxylic acid moieties are laurate, linoleate and behenate in a 1:3:4 molar ratio. A preferred solid material is sucrose polyester in which the degree of esterification is 7-8, and in which the fatty acid moieties are $C_{18}$ mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. Nos. 2,831,854, 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety. The emollient is, preferably, present at a concentration of from about 1% to about 20%, more preferably at from about 1% to about 10%.

Humectants of the polyhydric alcohol-type may also be included as part of the conditioning component of this invention. Typical polyhydric alcohols include polyalkylene glycols and more preferably alkylene polyols and their derivatives, including propylene glycol, dipropylene glycol, tripropylene glycol, polyethylene glycol and derivatives thereof, sorbitol, hydroxypropyl sorbitol, erythritol, threitol, pentaerythritol, xylitol, glucitol, mannitol, hexylene glycol, 1,3-butylene glycol, 1,2,6-hexanetriol, glycerol, ethoxylated glycerol, propoxylated glycerol, sodium 2-pyrrolidone-5-carboxylate, soluble collagen, gelatin and mixtures thereof. The humectant is, preferably, present at a concentration of from about 1% to about 20%, and more preferably at from about 1% to about 10% where the ratio of emollient to humectant is from about 5:1 to about 1:5, preferably from about 1:1 to about 1:2.

Also useful herein are guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and mixtures thereof.

Compositions

The compositions of the invention are administered to improve the condition and health of mammalian skin.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the compositions of the invention may be essentially continuous over a pre-selected period of time or may be in a series of spaced doses. Local administration is generally contemplated.

To achieve the desired effect(s), the composition may comprise dosages of the chitosan, vitamin $B_3$ and vitamin C components of at least about 0.1 µg/kg to about 100 to 200 mg/kg, of about 1.0 µg/kg to about 30 to 50 mg/kg, about 10 µg/kg to about 10 to 20 mg/kg or about 50 µg/kg to about 1.0 to about 10 mg/kg of body weight, although other dosages may provide beneficial results. The amount administered will vary depending on various factors including, but not limited to, the disease, the weight, the physical condition, the health, the age of the mammal, and whether wound treatment or skin conditioning is to be achieved. Such factors can be readily determined by the clinician employing animal models or other test systems that are available in the art.

The compositions are prepared by combining the active ingredients in the appropriate concentrations. Other active or inactive agents selected by one of skill in the art can optionally be added. The absolute weight of a given active agent included in a unit dose can vary widely. For example, about 0.1 µg to about 5 g, or about 1.0 µg to about 1 g, or about 10 µg to about 500 mg, of at least one of the components (chitosan, vitamin $B_3$ or vitamin C) can be administered. Alternatively, the unit dosage can vary from about 0.01 µg to about 1000 µg, from about 0.1 µg to about 750 µg, from about 1 µg to about 1 mg, from about 10 µg to about 750 µg, from about 25 µg to about 600 µg, from about 50 µg to about 500 µg, or from about 75 µg to about 400 µg.

Daily doses of the compositions of the invention can vary as well. Such daily doses can range, for example, from about 0.001 mg/day to about 5 g/day, from about 0.1 mg/day to about 2 g/day, from about 1 mg/day to about 1 g/day, from about 5 mg/day to about 500 mg/day, from about 10 mg/day to about 100 mg/day, and from about 25 mg/day to about 50 mg/day.

The compositions of the present invention can comprise from about 0.1% to about 99.5% a dermatologically acceptable carrier within which the chitosan, vitamin C, vitamin $B_3$ and other components are incorporated to enable the active ingredients to be delivered to the skin at an appropriate concentration.

The carrier can thus act as a diluent, dispersant, solvent, or the like for the particulate material which ensures that it can be applied to and distributed evenly over the selected target at an appropriate concentration.

The carrier may contain one or more dermatologically acceptable solid, semi-solid or liquid fillers, diluents, solvents, extenders and the like. The carrier may be solid, semi-solid or liquid. Preferred carriers are substantially liquid. The carrier can itself be inert or it can possess dermatological benefits of its own. Concentrations of the carrier can vary with the carrier selected and the intended concentrations of the essential and optional components.

Suitable carriers include conventional or otherwise known carriers that are dermatologically acceptable. The carrier should also be physically and chemically compatible with the essential components described herein, and should not unduly impair stability, efficacy or other use benefits associated with the compositions of the present invention. Preferred components of the compositions of this invention should be capable of being comingled in a manner such that there is no interaction that would substantially reduce the efficacy of the composition under ordinary use situations.

The type of carrier utilized in the present invention depends on the type of product form desired for the composition. The topical compositions useful in the subject invention may be made into a wide variety of product forms such as are known in the art. These include, but are not limited to, lotions, creams, gels, sticks, sprays, ointments, pastes, mousses and cosmetics (e.g., solid, semi-solid, or liquid make-up, including foundations, eye-makeup, pigmented or non-pigmented lip treatments, e.g., lipsticks, and the like). These product forms may comprise several types of carriers including, but not limited to, solutions, aerosols, emulsions, gels, solids, and liposomes.

For example, such carriers can contain a dermatologically acceptable, hydrophilic diluent. As used herein, "diluent" includes materials in which the particulate material can be dispersed, dissolved, or otherwise incorporated. Nonlimiting examples of hydrophilic diluents are water, organic hydrophilic diluents such as lower monovalent alcohols (e.g., $C_1$-$C_4$ alcohols) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof Water is a preferred diluent. The composition preferably comprises from about 60% to about 99.99% of the hydrophilic diluent.

Solutions according to the subject invention typically include a dermatologically acceptable hydrophilic diluent. Solutions useful in the subject invention preferably contain from about 60% to about 99.99% of the hydrophilic diluent.

Aerosols according to the subject invention can be formed by adding a propellant to a solution such as described above. Exemplary propellants include chloro-fluorinated lower molecular weight hydrocarbons. Additional propellants that are useful herein are described in Sagarin, Cosmetics Science and Technology 2nd Edition, Vol. 2, pp. 443-465 (1972), incorporated herein by reference. Aerosols are typically applied to the skin as a spray-on product.

Some carriers contemplated by the invention comprise an emulsion comprising a hydrophilic phase comprising a hydrophilic component, e.g., water or other hydrophilic diluent, and a hydrophobic phase comprising a hydrophobic component, e.g., a lipid, oil or oily material. As is known to one skilled in the art, the hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions typically comprise from about 1% to about 50% of the dispersed hydrophobic phase and from about 1% to about 98% of the continuous hydrophilic phase; water-in-oil emulsions typically comprise from about 1% to about 98% of the dispersed hydrophilic phase and from about 1% to about 50% of the continuous hydrophobic phase. The emulsion may also comprise a gel network, such as described in "Application of Emulsion Stability Theories to Mobile and Semisolid Oil-in-Water Emulsions", Cosmetics and Toiletries, vol. 101, November 1986, pp. 73-92, which is incorporated by reference herein. Preferred emulsions are further described below.

The topical compositions of the subject invention, including but not limited to lotions and creams, may comprise a dermatologically acceptable emollient. Such compositions preferably contain from about 2% to about 50% of the emollient. Emollients tend to lubricate the skin, increase the smoothness and suppleness of the skin, prevent or relieve dryness of the skin, and/or protect the skin. Emollients are typically water-immiscible, oily or waxy materials. A wide variety of suitable emollients are known and may be used herein. Sagarin, Cosmetics, Science and Technology, 2nd Edition, Vol. 1, pp. 32-43 (1972), incorporated herein by reference, contains numerous examples of materials suitable as an emollient.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80%, water. A cream typically comprises from about 5% to about 50%, preferably from about 10% to about 20%, of emollient; and from about 45% to about 85%, preferably from about 50% to about 75%, water.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, Cosmetics, Science and Technology, 2nd Edition, Vol. 1, pp. 72-73 (1972), incorporated herein by reference, and/or an emollient. For example, an ointment may comprise from about 2% to about 10% of an emollient; and from about 0.1% to about 2% of a thickening agent.

Compositions of this invention useful for cleansing ("cleansers") are formulated with a suitable carrier, e.g., as described above, and preferably contain one or more dermatologically acceptable surfactants in an amount that is safe and effective for cleansing. Preferred compositions contain from about 1% to about 90%, more preferably from about 5% to about 10%, of a dermatologically acceptable surfactant. The surfactant is suitably selected from anionic, cationic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, sodium lauryl sulfate, and betaines such as described herein. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in McCutcheon's Detergents and Emulsifiers, North American Edition (1986), published by Allured Publishing Corporation, which is incorporated herein by reference in its entirety. The cleansing compositions can optionally contain, at their art-established levels, other materials that are conventionally used in cleansing compositions.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier for the essential particulate material and may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter, incorporated herein by reference.

The compositions of the present invention are preferably formulated to have a pH of 10.5 or below. The pH values of these compositions preferably range from about 2 to about 10.5, more preferably from about 3 to about 8, even more preferably from about 5 to about 8.

Thus for topical administration, the compositions may be present as a solution, a suspension, an emulsion, a powder, a granular formulation, in a natural or synthetic polymer or resin, as a lotion, cream or paste.

The total active ingredients in such formulations comprise from 0.1 to 99.9% by weight of the formulation.

Formulations containing the therapeutic agents of the invention can be formulated with common excipients, diluents, or carriers, and formed into lotions, creams, solutions, suspensions, powders, aerosols, emulsions, salves, ointments and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

One of skill in the art may add adjuvants such as, for example, antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Furthermore, the active ingredients may also be used in combination with other therapeutic agents, for example, antimicrobial agents, pain relievers, anti-inflammatory agents, and the like, whether for the conditions described or some other condition.

The invention is further illustrated by the following non-limiting Examples.

EXAMPLE 1

Stimulation of Fibroblast Growth by Chitosan, Ascorbic Acid and Niacinamide The proliferative response of compositions containing chitosan, ascorbic acid, and niacinamide on the human skin fibroblast cell line was tested.

Materials and Methods

A human skin fibroblast cell line was obtained from Clonetics (Walkersville, Md., normal human dermal fibroblasts, neonatal). Stock solutions of CNA were prepared with chitosan (0.0297M, degree of deacetylation 78.8%, Vanson Inc.) and equimolar amounts of ascorbic acid and niacinamide (0.01649M, Sigma Chemical Co.) in water. Test solutions of chitosan (0.0297M) and niacinamide ascorbate (0.01649M) were separately prepared. All the compounds were tested at two doses, 5 and 10 ul with n=5. DMEM was used as a negative control (n=5).

The proliferative response of CNA, chitosan and NA, on the human skin fibroblast cell was measured in a 96-well assay system using serum-free DMEM (Dulbecco's Modified Eagle's Medium, Sigma Chemical Co.) as a control. Cells were seeded into 96 well plates at a concentration of $1 \times 10^3$ cells in 100 μl of DMEM containing 10% fetal bovine serum (FBS, Sigma Chemical Co., St. Louis, Mo.). Plates were incubated for 24 hours at 37° C. in a humidified 5% $CO_2$ atmosphere. After incubation, the medium was aspirated and the wells were rinsed twice with 100 μl of serum-free DMEM. The final rinse was aspirated and 100 ul DMEM serum was added to each well before adding test compounds. All wells were incubated for 28 hours at 37° C. in a humidified, 5% $CO_2$ atmosphere. After incubation, 20 μl of Cell Titer 96 Aqueous One Solution (Promega) was added to all wells. The plates were swirled gently and placed back in the incubator for 90 minutes and spectrophotometric absorbance was read at 490 nm. Statistical analysis of data was performed by using one-way ANOVA. $P<0.05$ is considered significant while $P<0.001$ is considered as very very significant.

Results

As can be seen in FIG. 1, the addition of chitosan, ascorbic acid, and niacinamide (CNA) leads to increased growth of fibroblasts in a dose-dependent manner. Cells receiving 5 μl equimolar chitosan, ascorbic acid, and niacinamide (labeled CNA5 in FIG. 1) exhibited greater cell growth (OD about 0.8) than control cells that received serum-free medium cells (OD about 0.6). Cells receiving 10 μl equimolar chitosan, ascorbic acid, and niacinamide (labeled CNA10 in FIG. 1) exhibited even greater cell growth (OD about 1.1), a statistically significant difference compared to control cells that received serum-free medium cells (OD about 0.6).

Cells receiving 5 μl 0.1649 M niacinamide alone (labeled NA5 in FIG. 1), exhibited slightly less cell density (about 0.58) than control cells that received serum-free medium cells (OD about 0.61). Cells receiving somewhat more niacinamide (10 μl 0.1649 M niacinamide, labeled NA10 in FIG. 1), exhibited even lower cell density (about 0.50). Hence, by itself niacinamide appears depress fibroblast cell growth.

Cells receiving 5 μl 0.1649 M chitosan alone (labeled Chito5 in FIG. 1), exhibited slightly higher cell density (about 0.7) than control cells that received serum-free medium cells (OD about 0.61). Cells receiving somewhat more chitosan (10 μl 0.1649 M chtisan, labeled Chtio10 in FIG. 1), exhibited a somewhat higher cell density (about 0.72). Hence, by itself chitosan appears to mildly stimulate fibroblast cell growth.

However, the combination of chitosan, ascorbic acid, and niacinamide (CNA) leads to greatly increased cellular growth of fibroblasts, suggesting that the combination of chitosan, ascorbic acid, and niacinamide (CNA) acts synergistically to increase the growth of fibroblasts.

TABLE 1

Summary of Data

| Group | Number of Points | Mean | Standard Deviation | Standard Error of Mean | Median |
|---|---|---|---|---|---|
| Chitosan5 | 5 | 0.6868 | 0.01527 | 0.006829 | 0.6920 |
| Chitosan10 | 5 | 0.7080 | 0.01732 | 0.007746 | 0.7130 |
| NA5 | 5 | 0.5650 | 0.01623 | 0.007259 | 0.5630 |
| NA10 | 5 | 0.4826 | 0.01242 | 0.005555 | 0.4870 |
| CNA5 | 5 | 0.8104 | 0.02806 | 0.01255 | 0.8210 |
| CNA10 | 5 | 1.068 | 0.03628 | 0.01623 | 1.052 |
| Control | 5 | 0.6130 | 0.01565 | 0.007000 | 0.6060 |

Therefore, CNA had a statistically significant effect on fibroblast proliferation that was greater than the effect of chitosan on fibroblast proliferation. CNA showed no toxicity at the tested doses. Although the effect was statistically non-significant, niacinamide (NA) appeared to inhibit cellular growth in a dose dependent manner. Statistically, CNA at both concentrations performed significantly better than chitosan and niacinamide alone, indicating that CNA may act synergistically to promote cell growth.

EXAMPLE 2

Comparison of Prolierative Activities of CNA, Ascorbic Acid (AA) and Niacinamide This Example provides further data supporting a synergistic effect by CNA on cell proliferation.

A stock solution of CNA was prepared with chitosan (0.0297M) and equimolar amounts of ascorbic acid and niacinamide (0.01649M) in water. Test solutions of equimolar ascorbic acid and niacinamide (0.01649M) were prepared separately in water. All the compounds were tested at two doses, 5 and 10 ul with n=5. DMEM was used as a negative control (n=5).

The proliferative response of CNA, ascorbic acid and niacinamide, on the human skin fibroblast cell line (Clonetics, Walkersville, Md., normal human dermal fibroblasts, neonatal) was measured in a 96-well assay system using serum-free DMEM (Dulbecco's Modified Eagle's Medium, Sigma Chemical Co.) as a control. Cells were seeded into 96 well plates at a concentration of $1 \times 10^2$ cells in 100 µl of DMEM containing 10% fetal bovine serum (FBS, Sigma Chemical Co., St. Louis, Mo.). Plates were incubated for 24 hours at 37° C. in a humidified 5% $CO_2$ atmosphere. After incubation, the medium was aspirated and the wells were rinsed twice with 100 µl of serum-free DMEM. The final rinse was aspirated and 100 ul DMEM serum was added to each well before adding test compounds. All wells were incubated for 28 hours at 37° C. in a humidified, 5% $CO_2$ atmosphere. After incubation, 20 µl of Cell Titer 96 Aqueous One Solution (Promega) was added to all wells. The plates were swirled gently and placed back in the incubator for 90 minutes and spectrophotometric absorbance was read at 490 nm.

Statistical analysis of data was performed by using one-way ANOVA. $P<0.05$ is considered significant while $P<0.001$ is considered as very very significant.

Results

Table 2 illustrates that CAN has a synergistic effect on cellular proliferation as compared with ascorbic acid and niacinamide. Niacinamide did not show any statistical difference (ns=non-significant) as compared to the control at both doses tested. Ascorbic acid has some cell proliferating activity at the two doses tested.

TABLE 2

Summary of Data

| Group | Number of Points | Mean | Standard Deviation | Standard Error of Mean | Median |
|---|---|---|---|---|---|
| Ascorbic acid1 | 5 | 0.4002 | 0.005215 | 0.002332 | 0.3990 |
| Ascorbic acid2 | 5 | 0.4598 | 0.01851 | 0.008279 | 0.4510 |
| Niacinamide1 | 5 | 0.3108 | 0.009039 | 0.004042 | 0.3140 |
| Niacinamide2 | 5 | 0.3048 | 0.009524 | 0.004259 | 0.3070 |
| CNA1 | 5 | 0.5470 | 0.007842 | 0.003507 | 0.5490 |
| CNA2 | 5 | 0.7890 | 0.01837 | 0.008216 | 0.7980 |
| Control | 5 | 0.3302 | 0.01462 | 0.006538 | 0.3350 |

All publications cited herein are hereby incorporated by reference in their entirety.

What is claimed:

1. A topical composition comprising about 40% to about 60% chitosan, about 20 to about 30% ascorbic acid, and about 20 to about 30% of a vitamin $B_3$ compound, wherein the composition is formulated to counteract a sign of aging on skin.

2. A topical composition comprising about 40% to about 60% chitosan, about 20 to about 30% ascorbyl glucosamine, and about 20 to about 30% of a vitamin $B_3$ compound, wherein the composition is formulated to counteract a sign of aging on skin.

3. The composition of claim 2 wherein the vitamin $B_3$ compound is niacinamide.

4. The composition of claim 2, wherein the composition can increase cellular proliferation of fibroblasts.

5. The composition of claim 2 wherein the sign of aging is a fine superficial wrinkle, a coarse deep wrinkle, a large pore, an age spot, photodamage, scaliness, flakiness, dryness, sagging in skin, puffiness in skin around an eye, puffiness in skin around a jowl, loss of skin elasticity, loss of skin firmness, loss of skin tightness, loss of skin recoil from deformation, discoloration, blotching, sallowness, hyperpigmentation, keratoses, hyperkeratinization, elastosis or collagen breakdown.

* * * * *